US006634751B2

(12) United States Patent
Turner et al.

(10) Patent No.: US 6,634,751 B2
(45) Date of Patent: Oct. 21, 2003

(54) INTRAOCULAR LENS DERIVATION SYSTEM

(75) Inventors: Timothy N. Turner, West Jordan, UT (US); Charles R. Broadus, Bothell, WA (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/950,262

(22) Filed: Sep. 10, 2001

(65) Prior Publication Data

US 2003/0053025 A1 Mar. 20, 2003

(51) Int. Cl.$^7$ ............................................... A61B 3/10
(52) U.S. Cl. ........................................ 351/212; 623/6.11
(58) Field of Search ............................... 351/205, 206, 351/211, 212, 221; 600/452; 623/6.23, 6.34, 6.36, 6.11; 606/5

(56) References Cited

U.S. PATENT DOCUMENTS

| | | | | |
|---|---|---|---|---|
| 5,092,880 A | | 3/1992 | Ohmi | 623/6 |
| 5,165,415 A | * | 11/1992 | Wallace et al. | 600/452 |
| 5,282,852 A | | 2/1994 | Capetan et al. | 623/6 |
| 5,358,520 A | * | 10/1994 | Patel | 623/6.34 |
| 5,886,767 A | * | 3/1999 | Snook | 351/212 |
| 5,968,095 A | | 10/1999 | Norrby | 623/6 |

FOREIGN PATENT DOCUMENTS

WO    WO 01/11418 A1    2/2001

OTHER PUBLICATIONS

Paper ASCRS 1998: Does Keratometry Really Estimate Corneal Power? Authors: Timothy N. Turner, Ph.D. Date: Apr. 19, 1998, pp. 19.

J Cataract Refract Surgery—vol. 19 Nov. 1993 Title: The Hoffer Q formula: A comparison of theoretic and regression formulas Author: Kenneth J. Hoffer, M.D. pp.: 700–712.

J Cataract Refract Surgery—vol. 20, Sep. 1994 Title: Ultrasound volcities for axial eye length measurement Author: Kenneth J. Hoffer, M.D. pp.: 554–562.

J. Cataract Refract Surgery—vol. 23—Apr. 1997 Title: At the Forefront of the IOL Revolution Author: Cornelius D. Binkhorst, M.D. pp.: 306–307.

J Cataract Refract Surgery, vol. 19—Nov. 1993 Title: Phacoemulsification, capsulorhexis, and intraocular lens power prediction accuracy Authors: Thomas Olsen, M.D. and Howard Bimbel, M.D. pp.: 695–699.

J Cataract Refract Surgery—vol. 26—Aug. 2000 2000 ASCRS and ESCRS—Published by Elsevier Science Inc. Title: Clinical results using the Holladay 2 intraocular lens power formula Author: Kenneth J. Hoffer, M.D. pp.: 1233–1237.

J Cataract Refract Surgery—vol. 22—Jan. and Feb. 1996 Title: Evaluation of Intraocular lens power calculation formulas in the triple procedure Author: Charles W. Flowers, M.D., Stephen D. McLeod, M.D., Peter J. McDonnell, M.D., John A. Irvine, M.D., and Ronald E. Smith, M.D. pp.: 116–122.

(List continued on next page.)

*Primary Examiner*—George Manuel
(74) *Attorney, Agent, or Firm*—Michael L. Smith

(57) ABSTRACT

An intraocular lens derivation system 10 includes an eye surface measurement device 12 for measuring the shape and position of at least the anterior and a posterior corneal surfaces of the eye, a length measurement device 14 for measuring at least the axial length of the eye, and an IOL calculator 24, connected to devices 12 and 14, for accurately selecting the proper IOL using at least in the selection the measured anterior and posterior corneal surface information and the axial length of the eye.

32 Claims, 1 Drawing Sheet

OTHER PUBLICATIONS

J. Cataract Refract Surgery—vol. 23—Nov. 1997 Title: Standardizing constants for ultrasonic biometry, keratometry, and intraocular lens power calculations Author: Jack T. Holladay, M.D., MSEE pp.: 1356–1370.

Documenta Ophthalmologica 85: 223—242—1994 Title: Factors influencing the accuracy of the SRK formular in the intraocular lens power calculation Authors: Chris Kalogeropoulos, Miltiadis Aspiotis, Maris Stefaniotou and Konstantinos Psilas pp.: 223–242.

J Cataract Refract Surgery—vol. 18—Mar. 1992 Title: Sources of error in intraocular lens power calculation Author: Thomas Olsen, M.D. pp.: 125–129.

J. Cataract Refract Surgery—vol. 26—May 2000 Title: intraocular lens power calculations in patients with extreme myopia Authors: Roberto Zaldivar, M.D., Mitchell C. Shultz, M.D., Jonathan M. Davidorf, M.D. and Jack T. Hollday, M.D. pp.: 668–674.

A Manual for Ophthalmologiests & Biometrists—Third Edition Title: Lens Implant Power Calculation Authors: John A. Retzlaff, M.D., Donald R. Sanders, M.D., Ph.D., Manus Kraff, M.D.

* cited by examiner

INTRAOCULAR LENS DERIVATION SYSTEM

FIELD OF THE INVENTION

This invention relates to a system for deriving an intraocular lens (IOL), suited to a particular patient and for replacing their natural but diseased crystalline lens, and more specifically, to a system for deriving the power and other parameters defining the IOL, based on corneal surface measurements (both anterior and posterior) and ocular length measurements (lens thickness, lens position, and axial length) of the patient's eye.

BACKGROUND OF THE INVENTION

Everyone, if they live long enough, will develop cataracts, which are degenerative opacities in the normal crystalline lens that restrict vision and hence quality of life. The normal course of treatment is to surgically remove the cataractous lens and replace it with a synthetic intraocular lens (IOL). Although there are many IOL varieties, their function is the same: to bring images seen by a person into sharp focus on their retina without the aid of other forms of correction (spectacles or contact lenses). To do this, the IOL must have the proper optical power. Excessive power causes the image to form in front of the retina, while insufficient power causes the image to form behind the retina. Only when the image focuses on the retina can the image appear sharp.

There are two major classes of IOLs in current use: spheric and toric. Toric IOLs can correct for astigmatism, which is the optical aberration characterized by a 2-fold sinusoidal variation of power with meridional angle. Persons having "with the rule" astigmatism have their greatest power aligned primarily in their infero-superior (i.e., vertical) plane, while persons having "against the rule" astigmatism have greatest power aligned primarily in their naso-temporal (i.e., horizontal) plane. Fewer patients have oblique alignments lying between the two more common extremes.

Spheric IOLs are characterized by a single power and can not correct for astigmatism. A third class of specialty IOLs is in limited clinical use and combines unusual features (like multi-focal power) to overcome special ocular defects (like presbyopia). A forth class of customized IOLs is not in clinical use but potentially could correct for higher order optical aberrations. There is a significant difference between specialty and customized IOLs. The latter attempts to provide a perfect optical image for a particular ocular state, while the former compromises image quality in an attempt to accommodate differing states of the eye.

Many factors contribute to the image that is delivered to and focused on the retina. Portions of the eye affecting this image include the cornea, the crystalline lens, the aqueous and vitreous humors within the eye, retinal shape, and the superficial tear film covering the cornea. In addition, optical focus is affected by both the shape (curvature, in particular) and location of all internal refracting surfaces, the refractive indices of the intervening material, as well as the axial length of the eye as a whole.

Much work has been done by many researchers to provide both theoretical and empirical formulas for calculating the IOL power suited to a particular patient. Clinically established IOL power formulas include SRK, SRK II, SRK/T, Holladay I, Holladay II, Binkhorst, Olsen, Hoffer-Calenbrander, TMB, DKG, and WPC formulas. Retzlaff, et al. in their book, *Lens Implant Power Calculation*, extensively discuss many lens power calculation formulas and the factors influencing the power calculation.

The IOL power calculation formulas listed above take into account many factors such as corneal curvature, anterior chamber depth, corneal size in terms of horizontal-white-to-white distance, anterior chamber depth, crystalline lens thickness, and the axial length of the eye. However, these formulas also estimate corneal power solely from measurements of the keratometric curvature (K) of the anterior corneal surface, which is a single number (or two in the case of astigmatism) typically measured by a keratometer. No information concerning the actual posterior corneal power is included in these formulas.

The details of how K is employed vary from formula to formula. For example in SRK, K is just a parameter in a regression analysis of the data. Holladay, on the other hand, tries to estimate the actual corneal power from K. This is done by assuming the posterior radius is exactly 1.2 mm smaller than the anterior radius deduced from K (see the *Journal of Cataract and Refractive Surgery*, volume 23, pages 1360–1361, November 1997). Although Holladay's approach may seem more satisfying, in that posterior power is not ignored, no more information is really added. Because empirical information is always used to tune each formula, the effect of posterior power is included automatically, but only for the normal, population-averaged, cornea.

Not accounting for the actual power of posterior cornea introduces the potential for error in the IOL derivation. Only when the posterior cornea closely follows the anterior cornea, which admittedly constitutes the majority of cases, is this neglect tolerable. However, when the posterior cornea diverges significantly from its anterior surface, the final surgical result is a "refractive surprise" that could only have been anticipated had the posterior corneal surface been measured and its power properly taken into account.

Another simplification that introduced error in the power calculation is not accounting for localized wave speed, interface refraction, and alignment of the optical and acoustic probe beams employed in ocular measuring devices. In humans, the line of sight is not generally aligned along the optical axis of the eye, but is often skewed several degrees from the optical axis. Light and sound probe beams not only refract at the tilted interfaces, but refract in opposite directions. This occurs because denser materials typically slow light while increasing sound speed. Also A-scan ultrasound instruments are typically aligned along the optical axis (giving the largest reflections), while optical instruments are aligned along the visual axis.

Another error-inducing simplification occurs when the retina is approximated as flat or uniformly receptive. Although a flat image plane is consistent with paraxial optics calculations, more sophisticated analyses that simulate the extended image (or point spread function) are affected by the curvature inherent in the photoreceptor surface. Spherical aberration is particularly affected. The long narrow shape of the photoreceptors gives them an angle dependent receptivity, not unlike a fiber optic. When taken as a whole, this is quantified by the well-known Stiles-Crawford effect.

A major failing of current technology is its inability to calculate IOL powers for eyes with non-normal corneas. These include all eyes compromised by corneal disease and corneal and refractive surgery. The fundamental problem stems from trying to assign a single curvature value (or two in the case of astigmatism) to a non-spherical surface. Keratometric curvature, the second most important parameter in current IOL power formulas, makes this assignment assuming the anterior corneal surface is spherical in shape. In actuality, the normal virgin cornea is prolate ellipsoidal, a difference whose consequences are hidden within the empirical constructs of these formulas. Post-operative corneas have distinctly different shapes, and therefore, they confound previous empiricisms. Such misshapen surface errors can only be corrected if the actual corneal shape (not just its keratometric curvature) is measured and properly taken into account.

Therefore, there is a need for a system where the actual measured corneal surfaces, both anterior and posterior, and the alignments, shapes, and positions of these and other important ocular components are used collectively in the derivation of the IOL that best fits a patient's eye.

BRIEF DESCRIPTION OF DRAWINGS

The FIGURE is a block diagram showing a system in accordance with the present invention.

DESCRIPTION OF PREFERRED EMBODIMENTS

Figure 1:
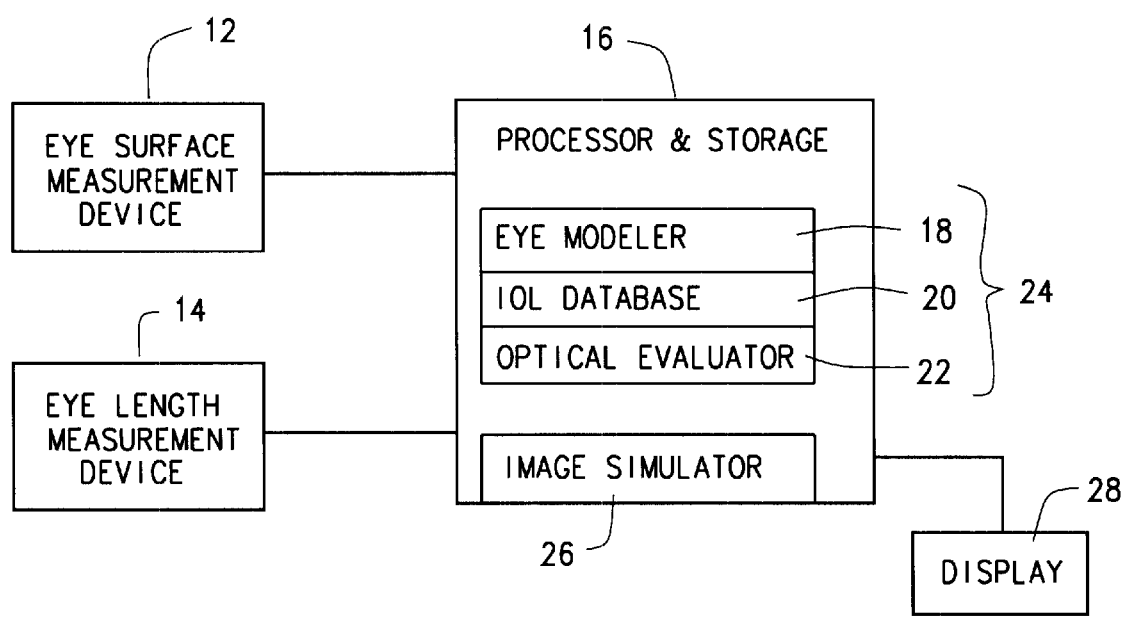

FIG. 1 shows an intraocular lens derivation system 10 including an eye surface measurement device 12 and an eye length measurement device 14, both connected to a central processing and storage device 16. Processor 16 further includes an eye modeler 18, an IOL database 20, an optical evaluator 22, and an image simulator 26. The eye modeler 18, IOL database 20, and the optical evaluator 22, can be taken together and referred to as an IOL calculator 24.

The surface measurement device 12 measures the shape and location of surfaces within an anterior segment of a patient's eye. At a minimum, these are the anterior and posterior corneal surfaces. Device 12 is preferably a corneal and anterior segment topography device, and more preferably is an Orbscan II instrument commercially available from Bausch & Lomb, Inc. Device 12 can also be a combination of known devices that can measure the shape and location of surfaces within the anterior segment of the eye.

The length measurement device 14 is preferably an ultrasound A-scan or B-scan device, but may be any combination of devices suited for measuring the ocular axial-length, and the crystalline lens position and thickness or even an optical measurement device.

The division of measurement functionality as shown in FIG. 1 and stated above is not important, because all the measurements will be combined by the eye modeler 18. For example, anterior chamber depth, the distance from the cornea to the anterior lens surface, may alternately be deduced from device 12, which measures surface locations within the anterior segment. Similarly, corneal thickness, which locates the posterior surface, may be determined by device 14, which measures ocular lengths.

The IOL calculator 24 determines the proper corrective lens for the eye by developing a plurality of customized eye models, each based on measurements from devices 12 and 14 and IOL data from data base 20, and then by optically evaluating each model with device 22.

The cataractous lens, whose optical influence is largely unknown and changes with time, is not part of any customized eye model. Rather, prospective IOL models are inserted in their prospective implanted positions and become part of the customized eye models. Each customized eye model differs from the others only in regards to the particular IOL model employed. An IOL model may be purely theoretical, or it may be a precise mathematical representation of an existing product, whose description is managed by the IOL database 20.

The primary function of the eye modeler 18 is to construct customized, self-consistent, ocular models that are consistent with the measured data. The eye modeler, with its grasp of all available data preferably, is able to compensate for inconsistencies and some omissions of data in measurements provided by devices 12 and 14. For example, as those skilled in the art will appreciate, once the surfaces and their orientations are established within the eye model, the model can be used to correct for interface refractions of the acoustic probe beams and the like. The eye modeler will also compensate for differences in interpretation between measurement technologies (primarily optical and acoustic). For example, the retinal boundary detected by ultrasound is offset from the optically sensing surface by a distance known in the art as the retinal thickness.

The preferred embodiment of the eye modeler uses conforming mathematical splines to capture the true shape of all optical interfaces 18 (at least anterior and posterior corneal surfaces and all IOL surfaces), as well as the shape of the retinal photoreceptor surface.

The evaluator 22, preferably optically evaluates each eye model using standard techniques (paraxial optics, raytrace optics, and/or diffraction optics) and grades them based on a metric. This metric may be an optical wavefront, or a point spread function (PSF), or some function derived from the optical wavefront or PSF, or any other metric that may be used to determine if a proper lens has been chosen. Not all possible eye models need be evaluated. Ordering of the different eye models (e.g., by the IOL power) and comparison with of the metric allows iterative search with local correction that often can be completed quickly in log time rather then linear time. Evaluator 22 may also employ geometric evaluations, (e.g., benefit curvature of the corneal surfaces) rather than the preferred optical evaluations.

The preferred embodiment of the optical evaluator 22 uses raytrace optics to calculate the wave aberration and diffractive optics to calculate the focused image characterized by the PSF. The preferred embodiment traces all rays admitted by the pupil and evaluates the PSF on a curved surface approximating the curvature inherent in the photoreceptor surface. The preferred embodiment weights all rays according to the Stiles-Crawford effect.

The preferred metric used by the optical evaluator 22 is based on the optical PSF, as this is most representative of the actual image falling upon the retina. The preferred metric also includes algorithms or processing functions to mimic the mental processing of the retinal image. As noted by many, our eye is a poor optical instrument connected to the best image processor in existence—the human brain. Much of our competence in seeing is based on the brain's ability to extract the relevant signal from a poor image, plagued by scattering, glare, and aberration—chromatic and otherwise. For example, presbyopia, or loss of accommodation with age, is often remedied with multi-focal lenses that simultaneously impress both blurry and sharp images on the retina. This works because of the brain's ability to filter out the blur and see the sharp image. In like manor, the preferred metric of the PSF must mimic the brain in filtering out blur in favor of sharpness. This can be accomplished with standard image processing algorithms and techniques.

Once the PSF has been calculated for the selected IOL, the PSF can be used to generate a simulated retinal image by standard techniques. This image will allow the doctor and patient to see and understand the predicted result of the implantation before surgery. Such information is especially beneficial when trying to choose a specialty IOL, as it will give the patient the opportunity to see the optical compromise offered by the specialty IOL.

There are two preferred embodiments of the IOL calculator 24, each having a different range of validity. The "normal" embodiment is valid only for eyes with normal corneas uncompromised by disease and surgery. The "general" embodiment is valid for all eyes, compromised or not.

Details described so far apply to the general embodiment. Obviously, paraxial optical techniques are inadequate in the general embodiment as they cannot capture aberration. Also, the general calculation includes all light rays accepted by the pupil. Because the actual measured corneal surfaces are employed in the customized eye model, the actual PSF generated by this optical system can be accurately calculated even for post-surgical and otherwise compromised eyes. And because an accurate IOL model (not just power) is employed in the customized eye model, the actual PSF generated by this optical system can be accurately calculated for all four classes of IOLs: spheric, toric, specialty, and customized.

The more restrictive, or normal embodiment, of the IOL calculator builds on the numerous IOL power calculation formulas prevalent in the field, that have been validated by millions of cataract surgeries world-wide. Clinically established IOL power formulas include SRK, SRK II, SRK/T, Holladay I, Holladay II, Binkhorst, Olsen, Hoffer-Calenbrander, TMB, DKG, and WPC formulas. The normal embodiment of the invention corrects keratometric curvature (K) with information based on actual measurements of the posterior corneal surface. In essence, the keratometer derived K is customized by the measured posterior power of the patient. There are numerous ways to do this. The following is a specific example that relies on corneal surface measurements only for posterior power correction (anterior information is still based on the K value measured with a keratometer):

1. Measure $K_1$ with a keratometer. $K_1$ is the initial or uncorrected value that would have been used in the standard IOL formula of choice.
2. Determine the power of the anterior surface $A_1$ from $K_1$ using paraxial surface power relations ($n_K$=1.3375 is the standard keratometric index, $n_C$=1.376 is the refractive index of the cornea):

$$A_1 = \frac{n_C - 1}{n_K - 1} K_1$$

3. Determine the power of the posterior surface P from corneal surface measurements using one of the following methods:
   3.1. From corneal surface measurements, compute full-pupil raytrace powers for the anterior cornea A, and the total cornea C (the latter includes both anterior and posterior surfaces). Then find the equivalent posterior power P by paraxial power subtraction (t is the corneal thickness):

$$P = \frac{C - A}{1 - \frac{t}{n_C} A}$$

3.2. From posterior surface measurements, parametrically fit the posterior surface shape to a sphere, conoid, ellipsoid, of other mathematical surface. Then find the paraxial surface power from a surface radius $R_P$ ($n_Q$=1.336 is the refractive index of the aqueous humor):

$$P = \frac{n_Q - n_C}{R_P}$$

3.3. From posterior surface measurements, calculate a local curvature of the posterior surface and average it over the apparent pupil. Then find the paraxial surface power from an averaged posterior curvature:

$$P = (n_Q - n_C)\bar{\kappa}_P$$

4. Paraxially combine $A_1$ and P into the best estimate of the actual corneal power $C_2$.

$$C_2 = A_1 + P - \frac{t}{n_C} A_1 P$$

5. Determine $K_2$ from the normal K(C) relation. This step is necessary to recast the best estimate of the actual corneal power $C_2$ into a form usable by the standard IOL formula.

$$K_2 = K(C_2)$$

$K_2$, the corrected value of $K_1$, is inserted into the standard formula. For normal eyes, $K_1$ and $K_2$ are essentially identical. However, when the posterior surface is abnormal with respect to its anterior surface, $K_2$ corrects for this difference and avoids a refractive surprise.

The C(K) relation, and its inverse K(C), are nonlinear but monotonic functions that capture the relation between actual cornea power and keratometric curvature in the population of normal eyes. The C(K) relation is a fit to data, obtained following steps 1–4 above for a large population of normal eyes. For an example of these data, see Turner, T. N. (April 1998) "Does keratometry really estimate corneal power", slide 16, in *Orbscan Presentations, October* 2000 *Edition*, available from Bausch & Lomb. It is believed the C(K) relation may be age, gender, and race localized.

The more restrictive or normal embodiment of the invention, includes all the parts of the general embodiment: eye modeler 18, IOL database 20, optical evaluator 22, and image simulator 26. In the example above, the eye model included only the cornea and did not use the IOL database. However, because the PSF is modified by the implanted IOL in more ways than just defocus, a more accurate solution can be obtained by including the IOL in the eye model. The IOL would be selected by the surgeon based on the uncorrected solution given by the standard power formula of choice. The model definition is then retrieved from the IOL database and incorporated in the eye model. Next, the optical evaluator determines the location of the optimum focal plane, which is necessary in the calculation of the system power. In this three element system, extraction of the posterior power P is more complex than the algorithm given in step 3.1, but it is still a paraxial operation. Finally, using the calculated PSF, the image simulator can display a simulated retinal image incorporating the selected IOL on display 28.

It is noted that the use of paraxial optics in translating and combining powers (e.g., in steps 2, 3, and 4 above) is justified only within the context of the more restrictive or normal embodiment, which must interface with existing IOL formulas. This is consistent with the theoretical justifications of all such formulas, which are grounded in paraxial optics, and is fundamentally consistent with the use of power, which is a paraxial concept.

The more restrictive normal embodiment of the invention can derive IOLs of all classes that can be derived by the standard formulas, that is, spheric, toric, and specialty IOLs. Custom IOLs, on the other hand, should employ the general embodiment, as no paraxial approximation should be used when attempting to correct higher order aberrations.

Many alternatives and variations to the Preferred Embodiments will be apparent to those skilled in the art without departing from the spirit and scope of the invention.

We claim:

1. An intraocular lens derivation system comprising:
   an eye surface measurement device for measuring an anterior segment of a patient's eye including an anterior and posterior corneal surface of the eye;
   an eye length measurement device for measuring an axial length of the eye, a crystalline lens thickness and position, and a corneal thickness;
   an eye modeler connected to each of the measurement devices for deriving a model of the eye based on the measured anterior and posterior corneal surfaces, the measured crystalline lens thickness and position, the measured axial length, the corneal thickness, and an IOL model;
   an IOL database for providing a technical description of the IOL model for use in the eye modeler;
   an optical evaluator for evaluating a plurality of eye models each including the model of a different IOL; and
   a metric for determining the success of the optical evaluation.

2. The system of claim 1 wherein the eye surface measurement device is a corned topography device.

3. The system of claim 1 wherein the eye surface measurement device is an Orbscan® device.

4. The system of claim 1 wherein the eye length measurement device is an A-scan device.

5. The system of claim 1 wherein the eye length measurement is a B-scan device.

6. The system of claim 1 wherein the optical evaluator includes ray tracing software.

7. The system of claim 1 further including an image simulator for displaying a simulated retinal image Incorporating a selected IOL.

8. An intraocular lens evaluation system comprising:
   an eye surface measurement device for measuring an anterior chamber of a patient's eye including an anterior and a posterior corneal shape of the eye, and an anterior chamber depth of the eye;
   an eye length measurement device for measuring length of the eye and a lens thickness;
   an intraocular lens (IOL) calculator operably connected to each of the eye measurement device and the eye length measurement device for calculating an IOL for the eye, using at least the measured anterior and posterior shape, the anterior chamber depth, and the length of the eye in the calculation; and
   an eye modeler operably connected to each of the measurement devices and the calculator for modeling the eye based on the measured anterior and posterior corneal shape, the anterior chamber depth, the measured eye length, the lens thickness, and the calculated IOL; and
   an evaluator for evaluating an eye model.

9. The system of claim 8 wherein the eye measurement device is a corneal topography device.

10. The system of claim 8 wherein the eye measurement device is an Orbscan® device.

11. The system of claim 8 wherein the eye axial-length measurement device is an A-scan device.

12. The system of claim 8 wherein the eye axial-length measurement is a B-scan device.

13. The system of claim 8 wherein the evaluator includes ray tracing software.

14. The system of claim 8 further including an image simulator for displaying a simulated retinal image incorporating a selected IOL.

15. An IOL calculator system comprising:
    an eye surface measurement device for measuring at least an anterior and a posterior corneal shape of an eye, and an anterior chamber depth of the eye; and
    an intraocular lens calculator operably connected to the eye measurement device for accurately calculating an IOL for the eye, using at least the measured anterior and posterior corneal shape and an axial-length of the eye in the calculation.

16. The system of claim 15 further including an eye axial-length measurement device for measuring the axial-length of the eye operably connected to the corrective lens calculator wherein the measured eye axial-length is used in the calculation.

17. The system of claim 15 wherein the eye measurement device is a corneal topography device.

18. The system of claim 17 wherein the eye measurement device is an Orbscan®device.

19. The system of claim 15 wherein a keratometry (k) factor and a corneal radius of curvature (r) factor in a known IOL power calculation formula is derived based on the measured anterior and posterior corneal curvature and forms a portion of the corrective lens calculator.

20. The system of claim 19 wherein the known IOL power calculation formula is taken from a group consisting of an SRK, SRKII, SRK/T, Holladay I, Holladay II, Binkhorst, Olsen, Hoffer-Calenbrander, TMB, DKG, and WPC formula.

21. The system of claim 15 further including an image simulator for displaying a simulated retinal image incorporating a selected IOL.

22. IOL calculator system comprising:
    an eye surface measurement device for measuring an anterior chamber of a patient's eye including an anterior and a posterior corneal shape of the eye, and an anterior chamber depth of the eye;
    an eye length measurement device for measuring an axial-length of the eye; and
    an IOL calculator operably connected to each of the eye measurement device and the eye length measurement device for accurately calculating a corrective lens for the eye, using at least the measured anterior and posterior shape, the anterior chamber depth, and the axial-length of the eye in the calculation.

23. The system of claim 22 wherein the eye measurement device is a corneal topography device.

24. The system of claim 23 wherein the corneal topography device is an Orbscan®device.

25. The system of claim 22 wherein a keratometry (k) factor and a corneal radius of curvature (r) factor in a known IOL power calculation formula is derived based on the measured anterior and posterior corneal curvature and forms a portion of the corrective lens calculator.

26. The system of claim 25 wherein the known IOL power calculation formula is taken from a group consisting of an SRK, SRKII, SRK/T, Holladay I, Holladay II, Binkhorst, Olsen, Hoffer-Calenbrander, TMB, DKG, and WPC formulas.

27. The system of claim 25 further including an image simulator for displaying a simulated retinal image incorporating a selected IOL.

28. The system of claim 22 wherein the eye axial-length measurement device is an A-scan device.

29. The system of claim 22 wherein the eye axial-length measurement device is a B-scan device.

30. A method of calculating an IOL power for a patient's eye, the method of comprising the steps of:

measuring an anterior chamber of the eye including measuring an anterior and a posterior corneal shape of the eye and an anterior chamber depth;

measuring an axial-length of the eye;

calculating the IOL for the eye using at least the measured anterior and posterior corneal shape, the anterior chamber depth, and the axial-length of the eye; and deriving a keratometry (k) factor and a corneal radius of curvature (r) factor for use in a known IOL power calculation formula wherein the k and r factor are based on the measured anterior and posterior corneal curvature.

31. The method of claim 30 wherein the known IOL power calculation formula is taken from the group consisting of as SRK, SRKII, SRK/T, Holladay I, Holladay II, Binkhorst, Olsen, Hoffer-Colenbrander, TMB, OKG, and WPC formulas.

32. The method of claim 30 further including an image simulator for displaying a simulated retinal image incorporating a selected IOL.

\* \* \* \* \*